United States Patent [19]
Schmedemann

[11] 3,933,251
[45] Jan. 20, 1976

[54] X-RAY EXAMINATION APPARATUS COMPRISING A COUNTER-WEIGHT FOR THE IMAGE SECTION

[76] Inventor: Walter Schmedemann, Timmerloh 3, 2 Hamburg 62, Germany

[22] Filed: May 15, 1974

[21] Appl. No.: 470,274

[30] Foreign Application Priority Data
May 16, 1973 Germany............................ 2324699

[52] U.S. Cl................................. 250/439; 250/444
[51] Int. Cl.².......................................... G03B 41/16
[58] Field of Search .......... 250/439, 444, 445, 446, 250/447, 448, 449; 269/323

[56] References Cited
FOREIGN PATENTS OR APPLICATIONS
1,204,929   1/1960   France................................ 250/444
1,051,979   12/1966   United Kingdom................. 250/444

Primary Examiner—Craig E. Church
Attorney, Agent, or Firm—Oblon, Fisher, Spivak, McClelland & Maier

[57] ABSTRACT

The invention relates to an X-ray examination apparatus comprising a counterweight for the image section which is movable in the compression direction.

The counterweight is suspended from the apparatus frame so as to be movable in the compression direction. Using a telescopic shaft and a system of belts and rollers, the counterweight acts to compensate for movements of the image section in the compression direction.

2 Claims, 3 Drawing Figures

X-RAY EXAMINATION APPARATUS COMPRISING A COUNTER-WEIGHT FOR THE IMAGE SECTION

The invention relates to an X-ray examination apparatus, comprising a principal carriage which is movable in the longitudinal direction of the apparatus frame and which accommodates a transverse carriage which is movable in the direction transverse to the longitudinal direction and which supports an image section (comprising inter alia the film cassette) which is movable in the compression direction (main direction of the X-rays), a counterweight being connected to the apparatus frame, the said counterweight being movable in the opposite sense with respect to the image section when the image section is moved in the compression direction, but remaining stationary when the image section is moved perpendicular to the compression direction because the transverse carriage incorporates a device for converting movement of the image section in the compression direction into rotation of a shaft which can be telescopically slid out but which is rotatable as one unit, a counterweight being coupled to the said shaft by way of a belt.

An apparatus of this kind is known from French Pat. Specification No. 1,204,929. In this known apparatus an additional sliding shaft and a set of crown wheels are provided between the belt connecting with the counterweight on the one side and the telescopic shaft on the other side. These provisions make the device comparatively complex and cause rather substantial friction during the movement of the principal carriage. The invention has for its object to provide a device in which there is no need for crown wheels and for an additional sliding shaft.

To this end, the device according to the invention is characterized in that on the transverse carriage the telescopic shaft, to which is fixed a belt drum, is journalled to be rotatable, the two ends of the belt being fastened to the belt drum such that when the drum rotates the belt ends are either both unwound or both wound, the belt extending from the one fastening point on the drum, in the longitudinal direction of the frame, to an 180° reversing guide roller provided on the frame near the one end thereof, subsequently returning in the said longitudinal direction to a 90° guide roller which is arranged to be rotatable near the other end of the frame, extending therefrom in the compression direction to an 180° reversing guide roller which is arranged to be rotatable on a counterweight which is movable in the compression direction, the belt subsequently returning in the compression direction to a second 90° guide roller, and finally extending in the longitudinal direction of the frame to the second fastening point on the drum, the arrangement being such that the image section and the counterweight move in opposite directions.

One embodiment according to the invention will be described in detail hereinafter with reference to the accompanying drawing.

Figure 1:
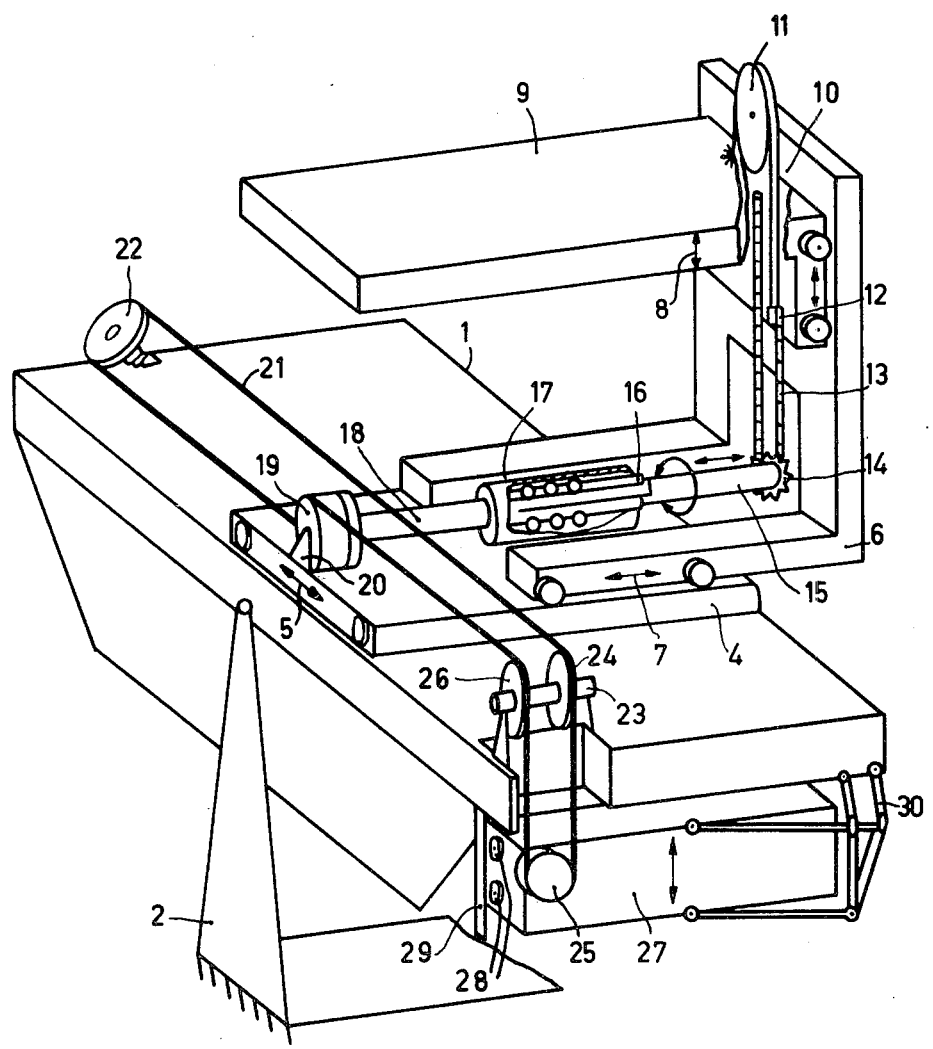
FIG. 1 is a diagrammatic view of an examination apparatus according to the invention.

The reference 1 in FIG. 1 denotes the frame of an X-ray examination apparatus which is journalled to be tiltable in a base 2. A principal carriage 4 can be displaced in the frame 1 of the apparatus in the longitudinal direction (direction of the arrow 5). The carriage 4 accommodates a transverse carriage 6 which can be displaced on the carriage 4 in the direction transverse to the longitudinal direction of the apparatus (direction of the arrow 7). Accommodated on the transverse carriage 6 is a carriage 9 which is slidable in the compression direction (direction of the arrow 8, i.e. in the main direction of the X-rays and perpendicular to the frame 1 of the apparatus) and which constitutes the image section of the apparatus which is not shown in detail. The guides for the rollers of the carriages 9, 6 and 4 have been omitted in the drawing for the sake of simplicity, and the weight compensation system for the longitudinal movement of the image section and of the carriage 4 has also been omitted for this reason. The X-ray tube and the patient table, both situated as usual in the space between the carriages 6 and 9, are not shown either. The carriage 9 has connected thereto the one end of a steel belt 10 which is guided over a roller 11, the shaft of which is permanently connected to the transverse carriage 6. The other end of the belt 10 is connected to a chain 13 at the point 12. The other end of the chain 13, guided over a gearwheel 14, is also connected to the image section 9. The gearwheel 14 is connected to a shaft 15 which is journalled to be rotatable on the transverse carriage 6 and which extends in the transverse direction, with the result that the tensile force exerted on the steel belt 10 and the chain 13 by the weight of the image section acts as a torque on the shaft 14.

The first shaft 15 comprises a central portion 16 which is provided with longitudinal ridges and which is envelopped by a sleeve 17 which is arranged coaxially thereabout and which is also provided with ridges. Provided in the ridges of the sleeve 17 and the portion 16 are spheres such that the torque is transferred from the first shaft 15 to the sleeve 17 and the first shaft 18 connected thereto, and that the first shaft 15 and the second shaft 18 are telescopically slidable in the axial direction relative to each other. Rigidly connected to the second shaft 18 is a drum 19 which is journalled on the principal carriage 4 at the point 20. The two ends of a belt 21, are permanently connected to the drum 19. The belt 21 passes from the drum 19 via an 180° reversing guide roller 22 which is journalled on or near the head end of the apparatus frame 1, via a 90° guide roller 24 which is journalled to be rotatable about a shaft 23 on or near the foot end of the frame 1, and via an 180° reversing roller 25 and a second 90° guide roller 26 which is journalled to be rotatable on the shaft 23 back to the drum 19 again. The belt 21 is secured to the drum 19 such that when the drum rotates the ends of the belt are either both wound or both unwound.

The roller 25 is rotatable about a shaft which is connected to a compensation weight (counter-weight 27). The counter weight 27 is guided by rollers 28 and a guiderail 29 such that the weight is slidable only in the compression direction. A parallelogram system of bars which is connected to the apparatus frame and to the counterweight 27 ensures that the counterweight 27 is not tilted during its upward or downward travel. The counterweight 27 is proportioned such that the torque exerted thereby on the drum 19 on the one side and the torque exerted on the gearwheel 14 by the image section 9 on the other side are equal but opposed.

The weight compensation in the compression direction upon movement of the image section 9 is effected as follows: during the upward or downward travel of the image section 9, the gear wheel 14 and hence also the drum 19 are rotated clockwise and counter-clockwise, respectively, the belt 21 then being wound onto and unwound from the drum 19, respectively. During the winding onto the drum, the belt ends guided via the rollers 26 and 24 simultaneously become shorter, with the result that the counterweight 27 is moved upwards, whilst during the unwinding from the drum the two belt ends simultaneously become longer and the counterweight is moved downwards. In both cases the guide roller 25 connected to the counterweight is not rotated, thus avoiding friction losses.

For the movement of the image section 9 in the transverse direction, only the transverse carriage 6 is moved, the sleeve 17 then telescopically sliding over the portion 16. The counterweight then remains immobile.

When the image section is moved in the longitudinal direction of the table, the carriage 4 is displaced without the drum being rotated. For example, when the carriage 4 is moved to the head end of the apparatus frame, the belt end guided via the roller 26 is pulled upwards, whilst the belt end guided via the roller 24 is pulled downwards to the same extent, with the result that the counterweight stays in its position when the image section 9 is moved in the longitudinal direction.

It is thus achieved, that the counterweight 27 — like in known apparatus — is moved only when the image section 9 is moved in the compression direction. The additional effort caused by the belt guide losses upon movement of the image section 9 is comparatively small, because a smaller number of guide rollers can be used. As is known (German Pat. Specification No. 1,048,668), additional means (not shown) can be provided which ensure that the counterweight is uncoupled from the image section when the examination apparatus is in the vertical position.

Figure 2:
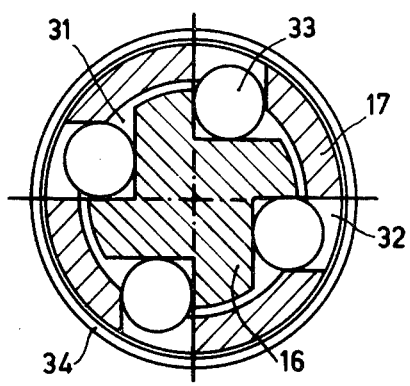
FIG. 2 shows an embodiment of a telescopic shaft member which is particularly suitable for an apparatus according to the invention.
Figure 3:
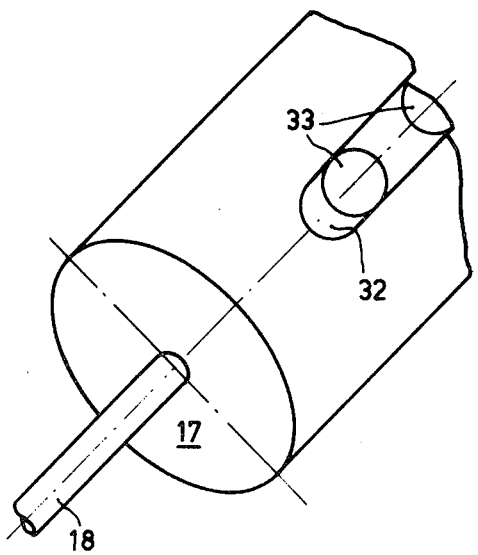
FIG. 3 shows a side elevation of the shaft member.

FIG. 2 is a detailed view of the sleeve 17 and the portion 16. The cylindrical shaft portion 16 is provided with four longitudinal grooves 31 which are shifted 90° with respect to each other. The sleeve 17 which concentrically envelops the shaft portion 16 is also provided with four grooves 32. The grooves 31 and 32 accommodate spheres, a spacer (not shown) being provided between the sleeve 17 and the shaft 16 to ensure that the spheres successively arranged in a ridge do not contact each other. A protective sleeve 34 (not shown in FIG. 3) about the sleeve 17 prevents the spheres from dropping out of the ridges. The arrangement shown in FIG. 2 constitutes a coupling in the direction of rotation between the sleeve 17 on the one side and the shaft portion 16 on the other side. The torque which can thus be transferred is particularly large when the torque on the sleeve 17 acts counter-clockwise, and that on the portion 16 clockwise. In view of the shape of the grooves, the torque which can be transferred counter-clockwise is smaller, but this is not a drawback in this case because the torque exerted by the counterweight 27 on the sleeve 17 and the torque exerted by the image section 9 on the shaft portion 16 each time act in only one direction. Moreover, the spheres in the grooves enable substantially friction-free telescopic sliding of the sleeve 17 with respect to the shaft portion 16 and hence of the shafts 15 and 18 with respect to each other.

What is claimed is:

1. X-ray examination apparatus comprising:
    a frame having a longitudinal direction, a transverse direction and a compression direction, all mutually perpendicular to each other;
    a principal carriage mounted on said frame for movement in the longitudinal direction;
    a transverse carriage mounted on said principal carriage for movement in the transverse direction;
    an image section mounted on said transverse carriage for movement in the compression direction;
    a first shaft rotatively mounted along the transverse direction on said transverse carriage;
    a second shaft rotatively mounted in the transverse direction on said principal carriage;
    means for mechanically coupling rectilinear movement of said image section in the compression direction to rotary movement of said first shaft;
    means for mechanically coupling rotary movement of said first shaft to rotary movement of said second shaft while permitting relative rectilinear movement thereof in the transverse direction;
    a belt drum coaxially mounted on said second shaft for common rotation therewith;
    a counterweight mounted on said frame for movement in the compression direction;
    a belt having two ends, both of which are attached to said drum, so that rotation of said drum simultaneously winds both ends of said belt onto or off of said drum thereby increasing or decreasing the remaining length of said belt, the ends of said belt extending away from each other in the longitudinal direction;
    a reversing guide roller mounted on said counterweight for reversing the direction of said belt; and
    guide rollers mounted on said frame for directing said belt toward and away from said reversing guide roller,
    whereby movement of said image section in the compression direction causes opposite movement of said counterweight in the compression direction, said counterweight counterbalancing the weight of said image section.

2. An x-ray examination apparatus as defined in claim 1 wherein said means for mechanically coupling rotary movement of said first shaft to rotary movement of said second shaft comprises a shaft portion coaxial with said first shaft and rigidly attached thereto for common rotation therewith, a sleeve coaxial with said second shaft and rigidly attached thereto for common rotation therewith, said shaft portion being coaxial with said sleeve and at least partly within said sleeve in a telescoping relationship, the inner surface of said sleeve and the outer surface of said shaft portion having corresponding grooves extending in the axial direction, and spheres held between said corresponding grooves and spacing said shaft portion and sleeve from each other, thereby preventing relative rotation of said sleeve and shaft portion while permitting telescoping movement thereof.

* * * * *

UNITED STATES PATENT AND TRADEMARK OFFICE
CERTIFICATE OF CORRECTION

PATENT NO. : 3,933,251
DATED : January 20, 1976
INVENTOR(S) : WALTER SCHMEDEMANN It is certified that error appears in the above—identified patent and that said Letters Patent are hereby corrected as shown below:

ON THE TITLE PAGE

Section [73] should be inserted as follows:

--[73] Assignee: U.S. PHILIPS CORPORATION, NEW YORK, N.Y.--

Section [56], Attorney identification should read as follows:

--Attorney, Agent, or Firm - Frank R. Trifari, Ronald L. Drumheller--

Column 2, line 39, "first shaft 18" should read

--second shaft 18--.

Signed and Sealed this

Second Day of November 1976

[SEAL]

Attest:

RUTH C. MASON
Attesting Officer

C. MARSHALL DANN
Commissioner of Patents and Trademarks